(12) United States Patent
Boo et al.

(10) Patent No.: US 10,662,140 B2
(45) Date of Patent: May 26, 2020

(54) METHOD FOR SKIN-WHITENING USING COMPOSITION CONTAINING RESVERATRYL TRIGLYCOLATE

(71) Applicant: KYUNGPOOK NATIONAL UNIVERSITY INDUSTRY-ACADEMIC COOPERATION FOUNDATION, Daegu (KR)

(72) Inventors: Yong Chool Boo, Daegu (KR); Won Choul Park, Seoul (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 258 days.

(21) Appl. No.: 15/347,229

(22) Filed: Nov. 9, 2016

(65) Prior Publication Data

US 2017/0210694 A1     Jul. 27, 2017

(30) Foreign Application Priority Data

Jan. 27, 2016   (KR) ........................ 10-2016-0010173

(51) Int. Cl.
| | | |
|---|---|---|
| *A61Q 19/02* | (2006.01) | |
| *A61K 8/37* | (2006.01) | |
| *C07C 69/73* | (2006.01) | |
| *C07C 69/675* | (2006.01) | |
| *C07C 67/08* | (2006.01) | |
| *A61Q 17/04* | (2006.01) | |

(52) U.S. Cl.
CPC ............. *C07C 69/73* (2013.01); *A61K 8/37* (2013.01); *A61K 8/375* (2013.01); *A61Q 19/02* (2013.01); *C07C 67/08* (2013.01); *C07C 69/675* (2013.01); *A61K 2800/782* (2013.01); *A61K 2800/805* (2013.01); *A61Q 17/04* (2013.01)

(58) Field of Classification Search
None
See application file for complete search history.

(56) References Cited

U.S. PATENT DOCUMENTS

2012/0149663 A1 *  6/2012  Brown ................... C07F 5/025
                                                                    514/64

FOREIGN PATENT DOCUMENTS

WO      WO-2017155875 A1 *  9/2017  ............... A61K 8/34

OTHER PUBLICATIONS

Park Soojin, Arch Dermatol Res (2016) 308:325-334. Published online: Mar. 30, 2016 (Year: 2016).*
J. Park et al., "Effects of Resveratrol, Oxyresveratrol, and Their Acetylated Derivatives on Cellular Melanogenesis", Springer-Verlag Berlin Heidelberg, Jan. 11, 2014, 306: 475-487.
G. Costin et al., "Human Skin Pigmentation: Melanocytes Modulate Skin Color in Response to Stress", The FASEB Journal, Sep. 2016, vol. 21, No. 4, pp. 976-994.
C.B. Lin et al., "Modulation of Microphthalmia-Associated Transcription Factor Gene Expression Alters Skin Pigmentation", The Society for Investigative Dermatology, Inc., Dec. 2002, vol. 119, No. 6, pp. 1330-1340.
Q. Liu et al., "Synthesis and Biological Evaluation of Resveratrol Derivatives as Melanogenesis Inhibitors", Molecules, Sep. 17, 2015, vol. 20, pp. 16933-16945.

* cited by examiner

*Primary Examiner* — Nicole P Babson
*Assistant Examiner* — Lori K Mattison
(74) *Attorney, Agent, or Firm* — McNees Wallace & Nurick LLC

(57) ABSTRACT

The present invention relates to a method for skin-whitening using a composition containing resveratryl triglycolate as an active ingredient, and more specifically, relates to a composition for skin-whitening containing resveratryl triglycolate or a cosmetically or pharmaceutically acceptable salt thereof as an active ingredient, a method for skin-whitening including applying or administering a composition containing resveratryl triglycolate or an acceptable salt thereof as an active ingredient to a subject, and a resveratryl triglycolate compound which has a skin-whitening effect, since the resveratryl triglycolate can inhibit melanin synthesis and brighten skin tone.

7 Claims, 5 Drawing Sheets

Specification includes a Sequence Listing.

[FIG. 1]
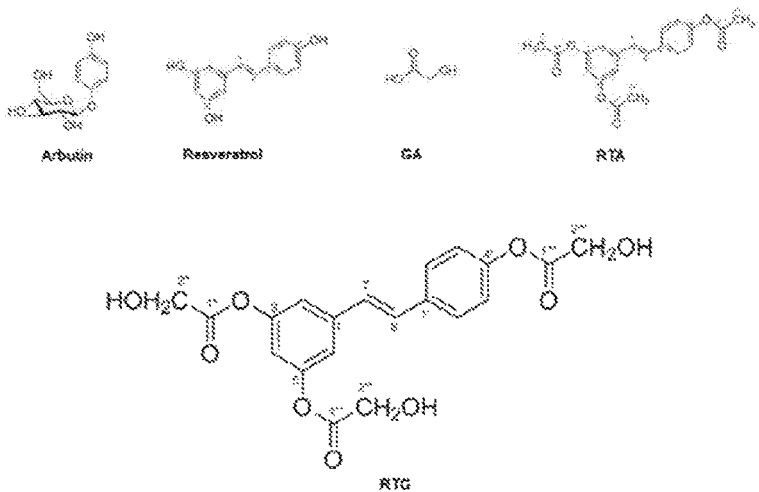
[FIG. 2]
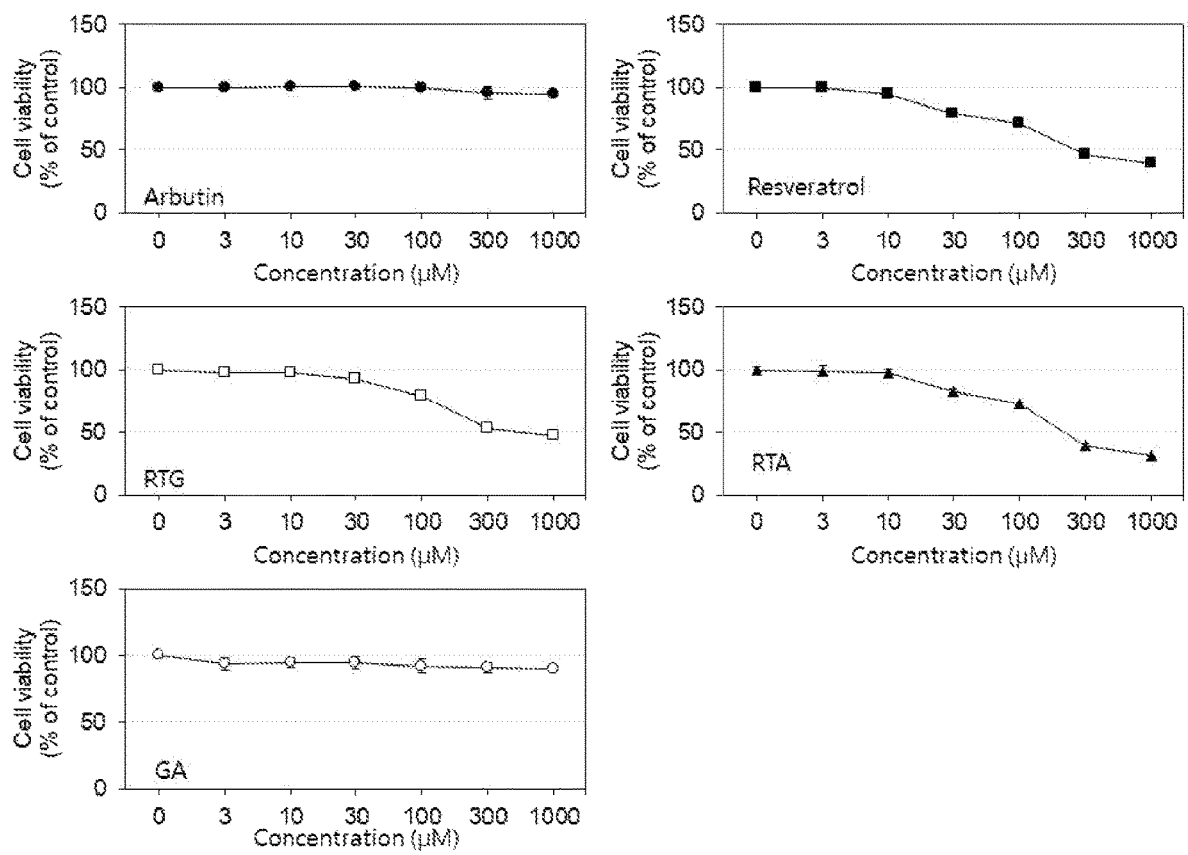

[FIG. 3]
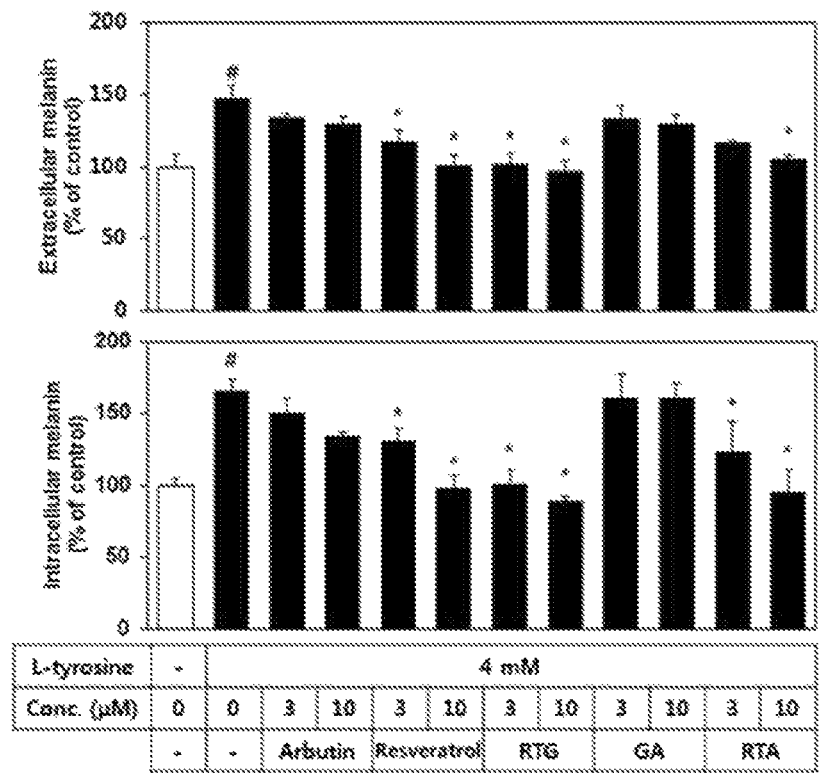
[FIG. 4]
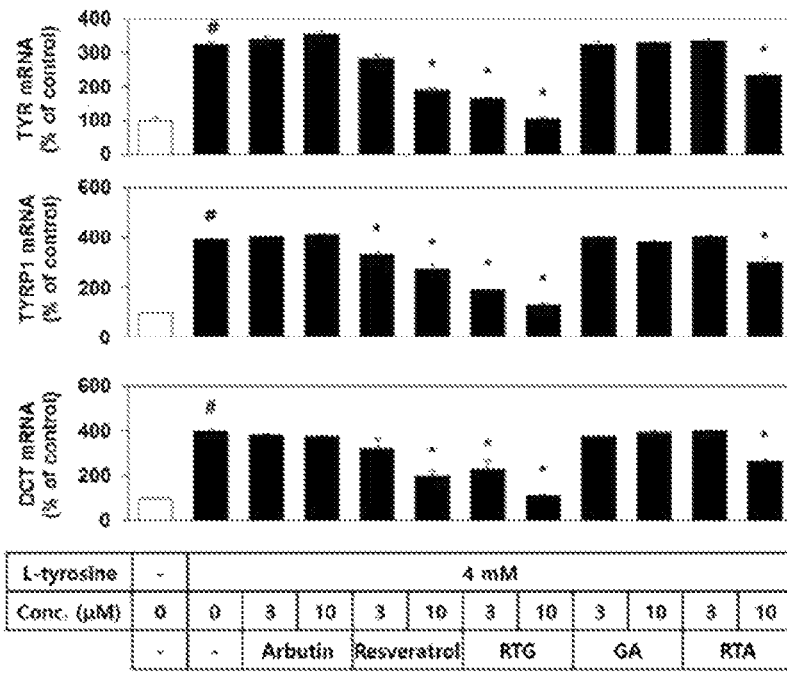

[FIG. 5]
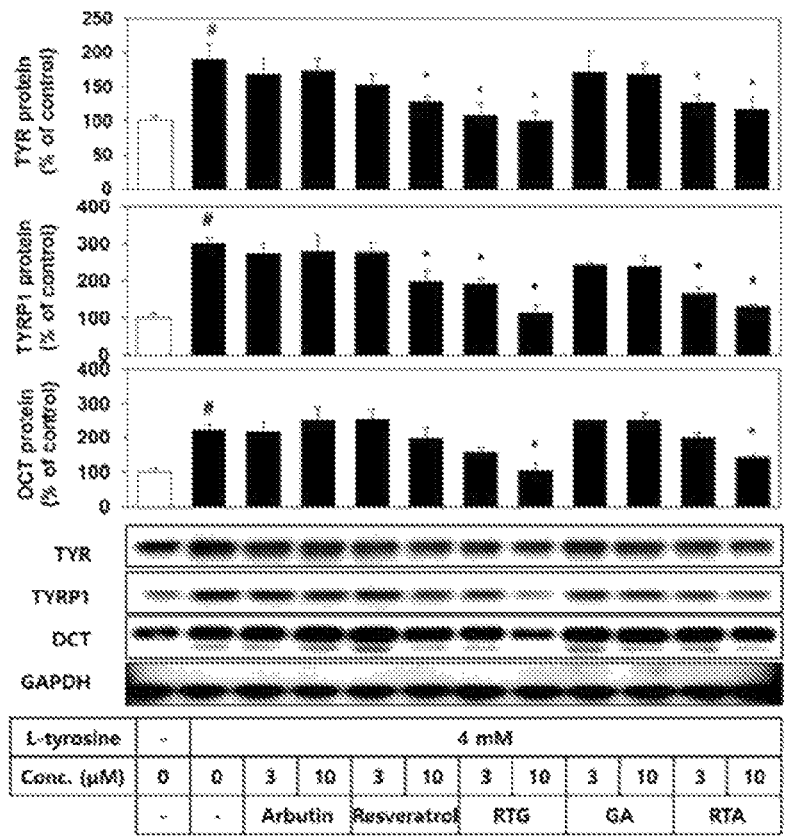
[FIG. 6]
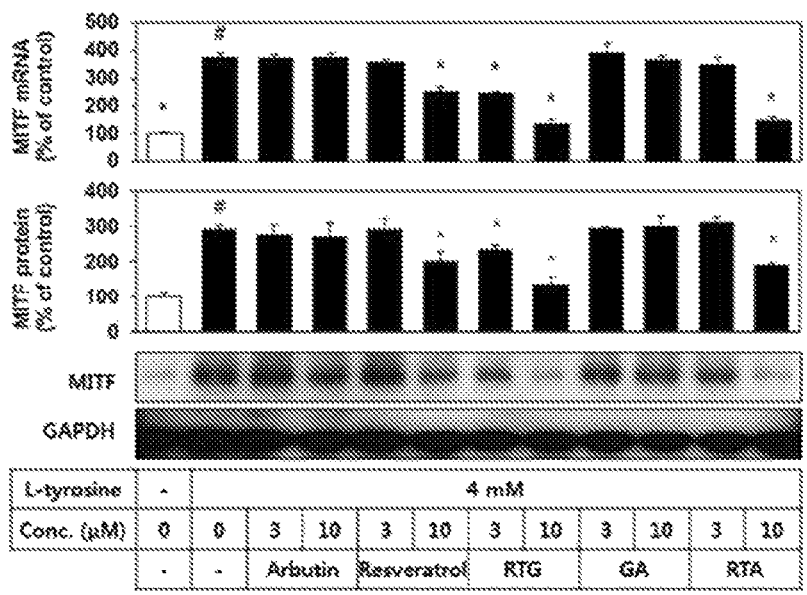

[FIG. 7]
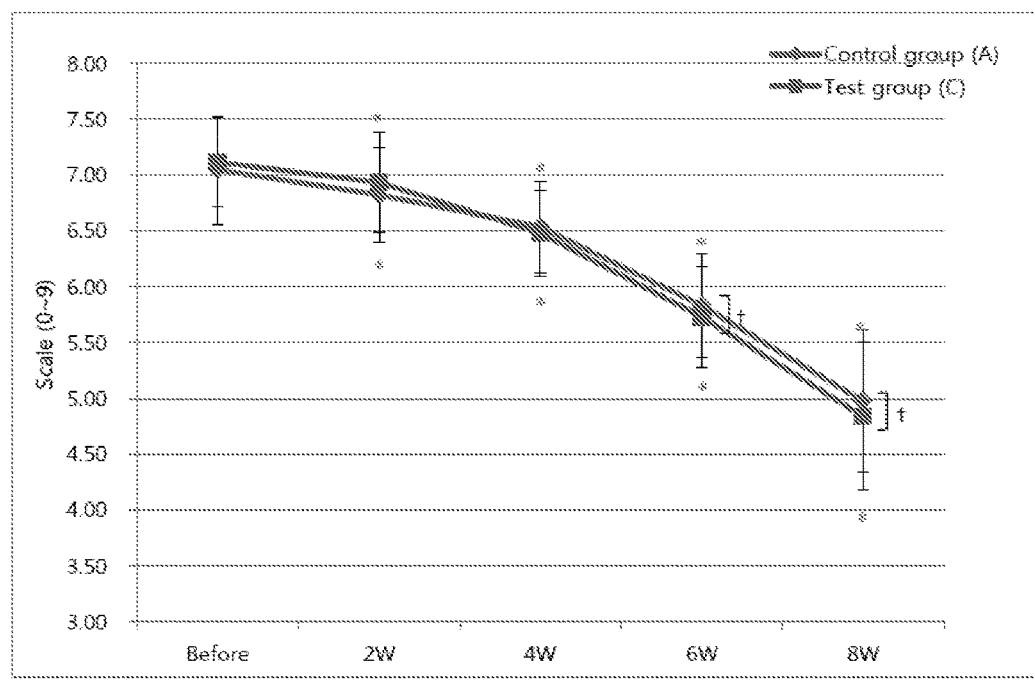
[FIG. 8]
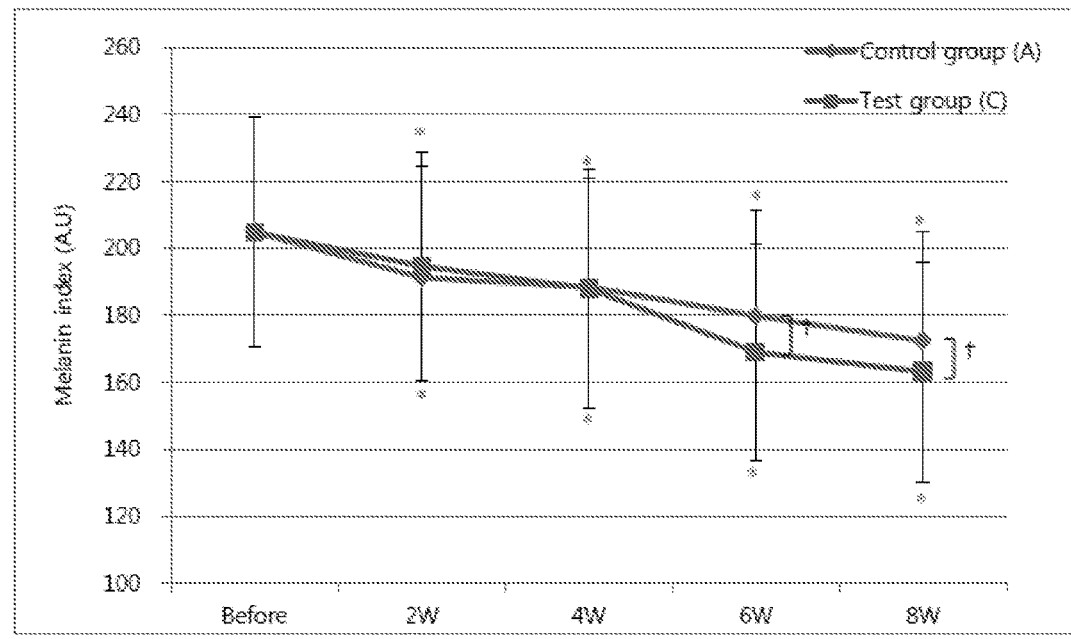

[FIG. 9]
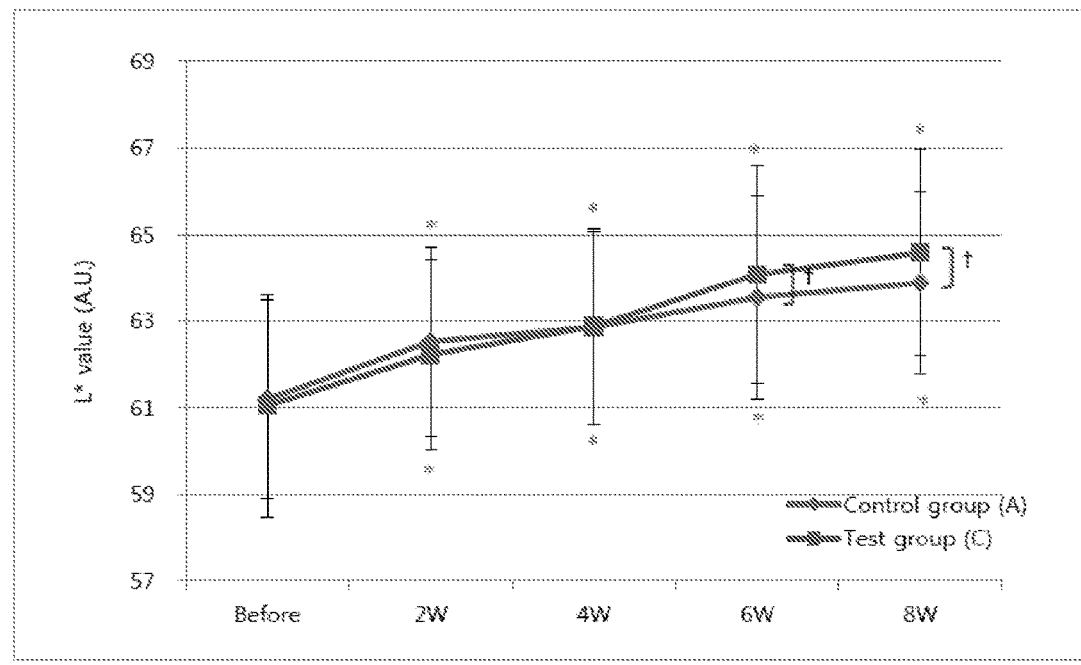
[FIG. 10]
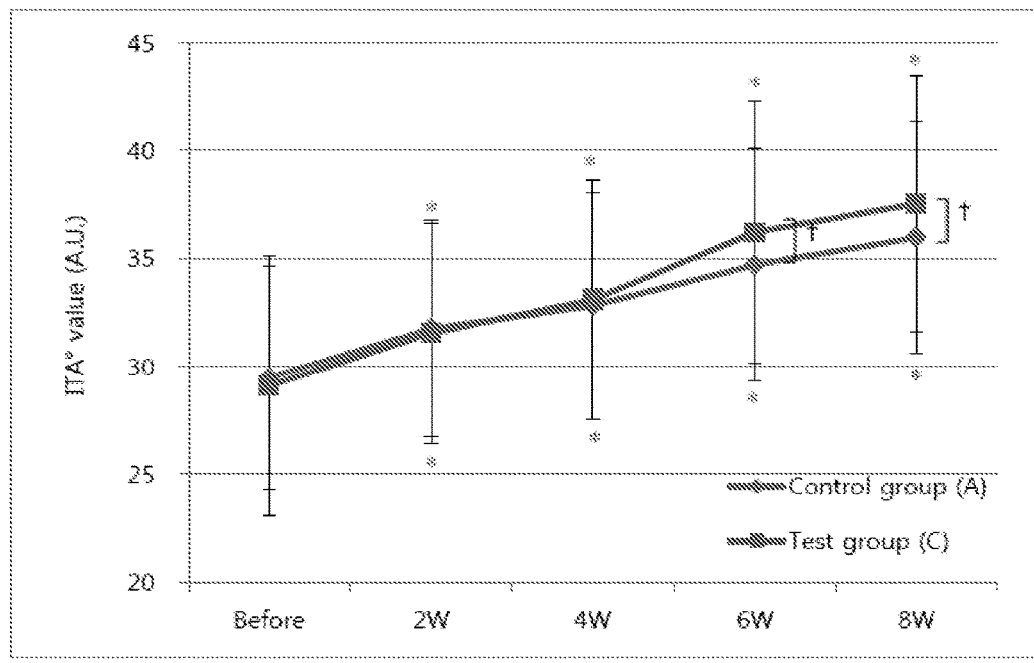

METHOD FOR SKIN-WHITENING USING COMPOSITION CONTAINING RESVERATRYL TRIGLYCOLATE

TECHNICAL FIELD

The present invention relates to a method for skin-whitening using a composition containing resveratryl triglycolate as an active ingredient, and more specifically, relates to a composition for skin-whitening containing resveratryl triglycolate or a cosmetically or pharmaceutically acceptable salt thereof as an active ingredient, a method for skin-whitening including applying or administering a composition containing resveratryl triglycolate or an acceptable salt thereof as an active ingredient to a subject, and a resveratryl triglycolate compound which has a skin-whitening effect.

BACKGROUND ART

Human skin color is genetically determined by the intracutaneous concentration and distribution of melanin, and is also affected by environmental or physiological conditions such as UV rays of the sun, fatigue, and stress.

Many studies have reported on the chemical effects of melanin synthesis. Melanin is produced by an organelle called a melanosome located in melanin-producing cells, melanocytes, and then transferred to keratinocytes. This melanin is known to protect the cells from UV light and is responsible for skin color.

The precursor of the melanin synthesis is an amino acid called tyrosine, which is known to be converted into dihydroxyphenylalanine (DOPA) and then dopaquinone, and finally results in the formation of melanin. Regarding the melanin biosynthesis, tyrosinase (TYR), tyrosine-related protein 1 (TYRP1) and dopachrome tautomerase (DCT) are known to contribute to melanin biosynthesis, and their major transcription factor, microphthalmia-associated transcription factor (MITF), also regulates melanin biosynthesis. Above all, TYR is known to have a critical role in melanin biosynthesis and is required for oxidation of tyrosine to DOPA and of DOPA to dopaquinone, and inhibition of TYR activity will lead to inhibition of melanin synthesis.

Among intrinsic components with a low molecular weight, a sulfhydryl agent containing sulfhydryl groups such as cysteine or reduced glutathione (GSH) has a role as a suppressor of TYR activity.

Meanwhile, the intracellular sulfhydryl agent not only suppresses the TYR activity, but also has an important role in the further metabolism of dopaquinone. Dopaquinone, an intermediate of melanin synthesis, may be converted into cysteinyldopa or glutathionyldopa by conjugation to cysteine or GSH, and their metabolites are converted into pheomelanin. In contrast to eumelanin, which is black or brown, pheomelanin is yellow or red, and a higher pheomelanin to eumelanin synthesis ratio results in yellow or red as the intensity of pigment becomes lower. The ratio of these two melanin pigments is a key factor in creating differences in skin color based on race. Additionally, it is known that reactive oxygen species (ROS), produced due to UV exposure, exhaust the intracellular sulfhydryl agent, thereby suppressing pheomelanin synthesis and promoting conversion into eumelanin.

Resveratrol is known to inhibit melanin synthesis as it suppresses the activity of MITF and TYR promoter in human epidermal melanocytes (Lin C B. et al., *J invest Dermatol* 2002; 119:1330-40). Accordingly, resveratrol decreases cellular melanin synthesis through multiple mechanisms, including inhibition of catalytic activity, gene expression, and posttranslational maturation of the TYR enzyme. Due to such effects of resveratrol, various chemical modifications have been attempted in order to enhance the utility of resveratrol.

The stability, safety, and efficacy of active ingredients are considered to be important in the cosmetic industry, but resveratrol is likely to be oxidized, thus making it difficult to be used as a cosmetic component which requires a long shelf life. Recently, the present inventors chemically modified resveratrol to produce resveratryl triacetate (RTA), and reported that the RTA, maintains higher stability to oxidation and is less toxic, compared to resveratrol, using a cultivated melanocytes and a reconstituted skin tissue model, and that it was an effective inhibitor of melanin synthesis, (Park J. et al., *Arch Dermatol Res* 2014; 306: 475-87). However, a formulation of a cosmetic or pharmaceutical composition is still difficult due to the solubility issues. The safety, toxicity, and efficacy of various active ingredients including resveratrol require further study.

The present inventors have made extensive efforts to seek an active ingredient having a skin-whitening effect, and as a result, they have confirmed that resveratryl triglycolate, produced by chemically modifying resveratrol, inhibits melanin synthesis, decreases expression levels of TYR, TYRP1, and DCT, and decreases MITF, thereby showing an excellent skin-whitening effect, thus completing the present invention.

DISCLOSURE OF INVENTION

Technical Problem

An object of the present invention is to provide a cosmetic composition for skin-whitening containing resveratryl triglycolate, represented by Formula I below.

[Formula 1]

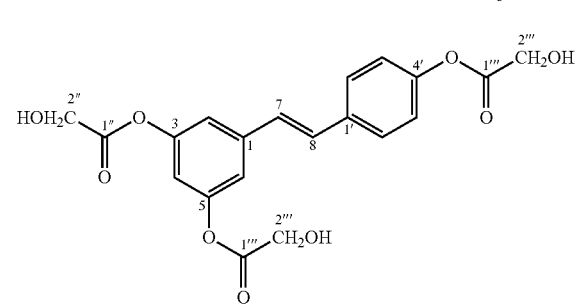

Another object of the present invention is to provide a pharmaceutical composition for skin-whitening containing resveratryl triglycolate or a pharmaceutically acceptable salt thereof as an active ingredient.

Still another object of the present invention is to provide a method for skin-whitening including applying or administering to a subject a composition containing resveratryl triglycolate.

Still another object of the present invention is to provide a resveratryl triglycolate compound which has a skin-whitening effect.

Technical Solution

In order to achieve the above objects, an aspect of the present invention provides a cosmetic composition for skin-whitening containing resveratryl triglycolate or a cosmetically acceptable salt thereof as an active ingredient.

In the present invention, the cosmetic composition containing resveratryl triglycolate inhibits melanin synthesis, thereby improving a skin-whitening effect.

As used herein, the term "resveratryl triglycolate" refers to a compound derived by esterification of resveratrol with tetrahydropyran (THP)-protected glycolic acid (GA).

In an embodiment of the present invention, (E)-5-(4-(2-(tetrahydro-2H-pyran-2-yloxy)acetoxy)styryl)-1,3-phenylene bis(2-(tetrahydro-2H-pyran-2-yloxy)acetate) was produced by esterification of resveratrol with tetrahydropyran-protected glycolic acid using 1-ethyl-3-(3-dimethylaminopropyl)carbodiimide (EDC) as a dehydration agent and 4-dimethylaminopyridine (DMAP) as a catalyst. The thus-obtained product was dissolved in dioxane and mixed with 2 N HO/ether to prepare resveratryl triglycolate as a white solid. Every step was confirmed by $^1$H and $^{13}$C NMR spectroscopy and mass spectrometry, and resveratryl triglycolate was obtained as amorphous powder.

The composition of the present invention may contain resveratryl triglycolate or a cosmetically acceptable salt thereof as an active ingredient. An acid addition salt, prepared by a cosmetically acceptable free acid, may be an effective salt. The acid addition salt may be prepared by a conventional method, for example, by dissolving the compound in an excess amount of an aqueous acid solution and precipitating the salt in a water-miscible organic solvent such as methanol, ethanol, acetone, or acetonitrile. Heating an equimolar amount of the compound and an aqueous acid solution or an alcohol (e.g., glycol monomethyl ether) followed by dehydrating the mixture by evaporation or filtrating the precipitated salt under vacuum filtration may also produce the acid addition salt. In particular, as the free acid, an organic or inorganic acid may be used; hydrochloric acid, phosphoric acid, sulfuric acid, nitric acid, stannic acid, and hydroiodic acid may be used as the inorganic acid, and methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, and vanillic acid may be used as the organic acid, although the free acid is not limited thereto.

Also, a cosmetically acceptable metal salt may be prepared using a base. An alkali metal or alkaline earth metal salt, for example, is prepared by dissolving a compound in an excess amount of an alkali metal hydroxide or alkaline earth metal hydroxide solution, filtering an undissolved compound salt, and then vaporizing and dehydrating the filtrate. In addition, a corresponding silver salt may be obtained by having an alkali metal or alkaline earth metal salt react with a suitable silver salt (for example, silver nitrate).

As used herein, the term "whitening" refers to prevention against hyperpigmentation of melanin in the skin due to an increase in the number of melanin cells through prolonged UV exposure, or a function to reduce melanin levels in the skin. Accordingly, it suppresses formation of melasma or freckles.

The cosmetic composition for skin-whitening according to the present invention may be formulated in a dosage form of an aqueous solution, suspension, emulsion, paste, gel, cream, lotion, powder, soap, surfactant-containing cleanser, oil, powder foundation, emulsion foundation, wax foundation, and spray.

The cosmetic composition for skin-whitening according to the present invention may include at least one additive selected from the group consisting of water, surfactant, humectant, low-grade alcohol, chelating agent, germicide, anti-oxidant, preservative, pigment, and fragrance.

The cosmetic composition of the present invention may contain the active ingredient at from 0.001 wt % to 5 wt % of the whole composition, specifically from 0.01 wt % to 5 wt %.

The cosmetic composition for skin-whitening according to the present invention may additionally contain a cosmetic excipient. Within the scope of not reducing the effect of the present invention, i.e., the skin-whitening effect, a known conventional ingredient such as a humectant, powder component, UV absorber, anti-oxidant, cosmetic component, glycolipid, plant extract, preservative, fragrance, pH adjuster, dye, viscosity modifier, and gelling agent may be included.

Examples of the humectant may include a glycol such as propylene glycol, isoprene glycol, 1,2-heptanediol, 1,3-butylene glycol, dipropylene glycol, hexanediol, polyethylene glycol glycerin, glycerin, diglycerin, triglycerin, polyglycerin, neopentyl glycol, sorbitol, erythritol, pentaerythritol, glucose, and galactose, fructose, sucrose, maltose, xylose, xylobiose, reductant of an oligosaccharide, protein, mucopolysaccharide, collagen, elastin, keratin, and triethanolamine, but are not limited thereto.

Examples of the powder component may include a white inorganic pigment such as titanium dioxide, silicone-treated titanium oxide, zinc oxide, and barium sulfate, a blue or colored inorganic pigment such as iron oxide, carbon black, and titanium oxide sinter, a white powder such as talc, siliconized talc, muscovite, kaolin, silicon oxide, bentonite, smectite, silicic acid anhydride, aluminum oxide, magnesium oxide, zirconium oxide, diatomite, calcium silicate, barium silicate, magnesium silicate, calcium carbonate, magnesium carbonate, hydroxyapatite, and boron nitride, an organic polymer resin powder such as titanium dioxide-coated mica, iron oxide mica titanium, silicon-treated mica titanium, mica titanium-treated silicon, fish scale flake, polyethylene resin, fluorine resin, cellulose resin, and silicone resin, an organic powder with a low molecular weight such as zinc stearate and N-acyl-lysine, a natural organic powder such as starch, silk powder, and cellulose powder, an organic pigment powder such as red No. 201, red No. 202, orange No. 203, orange No. 204, blue No. 404, and yellow No. 401, an organic pigment powder such as zirconium, barium, and aluminum lakes of red No. 3, red No. 104, red No. 106, orange No. 205, yellow No. 4, yellow No. 5, green No. 3, and blue No. 1, and a composite powder such as gold foil powder and fine titanium dioxide-coated mica titanium of mica and gold powder, but are not limited thereto.

Examples of the UV absorber may include a benzophenone derivative, p-aminobenzoate derivative, methoxycinnamate derivative, and urocanate, but are not limited thereto.

Examples of the antioxidant may include BHT, BHA, vitamin C, vitamin E, and derivatives and salts thereof, but are not limited thereto.

Examples of the cosmetic ingredient may include the vitamins of the antioxidant, derivatives and salts thereof, an anti-inflammatory drug, and a crude drug, but are not limited thereto.

Examples of the glycolipid may include sphingoglycolipid, but are not limited thereto.

Examples of the plant extract may include an extract of aloe vera, witch hazel, hamamelis, cucumber, lemon, lavender, and rose, but are not limited thereto.

Examples of the preservatives may include methyl p-hydroxybenzoate, ethyl p-hydroxybenzoate, butyl p-hydroxybenzoate, propyl p-hydroxybenzoate, phenoxyethanol, and ethanol, but are not limited thereto.

Examples of the fragrance may include camphor oil, orange oil, peppermint oil, jasmine absolute, pine oil, lime oil, lavender oil, rose oil, and musk oil, but are not limited thereto.

Examples of the pH adjuster may include edetate, sodium edetate, sodium chloride, citrate, sodium citrate, sodium anhydride, potassium anhydride, and triethanolamine, but are not limited thereto.

Examples of the dye may include blue No. 1, blue No. 204, red No. 3, and yellow No. 201, but are not limited thereto.

Examples of the viscosity modifier may include polyvinyl alcohol (PVA), methylcellulose (MC), ethyl cellulose, hydroxypropyl methylcellulose, hydroxypropyl ethyl cellulose and other cellulose derivatives, polyvinyl pyrrolidone (PVP), carboxymethylcellulose, xanthan gum, alginate or salts thereof, carrageenan, quince seed powder, alcaligenes polysaccharides, carboxyvinyl polymer, acrylic acid, acrylic acid polymers (chain, cross-linked), and alkyl methacrylate copolymer, but are not limited thereto.

Examples of the gelling agent may include (behenate/eicosadioate) glyceryl and (behenate/eicosanoate) polyglyceryl-10, metal salts of fatty acids, hydroxystearate, dextrin fatty acid esters, inulin fatty acid esters, sugar fatty acid esters, acylated cellobiose, dibenzylidene sorbitol, amino acid-based gelling agents, silicic acid anhydride, organically modified clay minerals, free silica, alumina, cross-linked organopolysiloxane, hydrocarbon wax such as polyethylene wax and paraffin wax, plant wax such as carnauba wax and candelilla wax, agar, and gelatin, but are not limited thereto.

The cosmetic composition of the present invention may be prepared in any dosage form which is conventionally used in the art, for example, an aqueous solution, suspension, emulsion, paste, gel, cream, lotion, powder, soap, surfactant-containing cleanser, oil, powder foundation, emulsion foundation, wax foundation, and spray, but the dosage form is not limited thereto.

Additionally, the cosmetic composition of the present invention may further include at least one cosmetically acceptable carrier which is well blended in a general skin cosmetic composition, for example, oil, water, surfactant, humectant, low-grade alcohol, thickening agent, chelating agent, dye, preservative, and fragrance may be blended therewith, but the carrier is not limited thereto.

An acceptable carrier contained in the cosmetic composition of the present invention may vary according to the dosage form. In a case where the dosage form of the present invention is a paste, cream, or gel, an animal oil, vegetable oil, wax, paraffin, starch, tragacanth, cellulose derivative, polyethylene glycol, silicon, bentonite, silica, talc, and zinc oxide may be used as a carrier.

In a case where the dosage form of the present invention is a powder or a spray, lactose, talc, silica, aluminum hydroxide, calcium silicate, and polyamide powder may be used as a carrier, and in particular, a propellant such as chlorofluorocarbon, propane/butane, and dimethyl ether may be further included in the spray.

In a case where the dosage form of the present invention is either an aqueous solution or an emulsion, solvent, solubilizing agent, or emulsifying agent such as water, ethanol, isopropanol, ethyl carbonate, ethyl acetate, benzyl alcohol, benzyl benzoate, propylene glycol, and 1,3-butyl glycol oil, particularly, cottonseed oil, peanut oil, corn germ oil, olive oil, castor oil and sesame oil, and glycerol aliphatic ester, may be used as a carrier.

Additionally, in a case where the dosage form of the present invention is a suspension, a diluent such as water, ethanol, and propylene glycol, and a suspension agent such as ethoxylated isostearyl alcohol, polyoxyethylene sorbitol ester, and polyoxyethylene sorbitan ester, as well as microcrystalline cellulose, aluminum meta-hydroxide, bentonite, agar, and tragacanth may be used as a carrier.

Additionally, in a case where the dosage form of the present invention is a surfactant-containing cleanser, an aliphatic alcohol sulfate, aliphatic alcohol ether sulfate, sulfosuccinate monoester, isethionate, imidazolinium derivative, methyl taurate, sarcosinate, fatty acid amide ether sulfate, alkylamido betaine, aliphatic alcohol, fatty acid glyceride, fatty acid diethanolamide, vegetable oil, lanolin derivative, and ethoxylated glycerol fatty acid ester may be used as a carrier.

As another aspect, the present invention provides cosmetics containing the cosmetic compositions.

According to subparagraph 1 of Article 2 of the Cosmetics Act, the "cosmetic" of the present invention refers to a product used on a human body in order to increase physical attractiveness by cleansing and beautifying the body, to improve the appearance, or to maintain or enhance the health of skin and hair, and considered to have an insignificant effect on the human body.

The cosmetic according to the present invention may refer to a functional cosmetic. The "functional cosmetic" of the present invention is defined in the Cosmetics Act as a cosmetic product of which a particular benefit and an effect are emphasized, as they aid in whitening of skin, improving wrinkles, tanning skin gently, and protecting skin from UV rays.

The cosmetic according to the present invention has been confirmed to have a skin-whitening effect when applied to a human body, and so is a functional cosmetic.

The cosmetic according to the present invention may be formulated in one of the following dosage forms: skin lotion, skin softening lotion, skin toner, astringent, lotion, milky lotion, moisturizing lotion, nutritive lotion, massage cream, nourishing cream, moisturizing cream, hand cream, essence, nutritive essence, pack, soap, shampoo, cleansing foam, cleansing lotion, cleansing cream, body lotion, body cleanser, milky liquid, pressed powder, loose powder, and eye shadow.

As another aspect, the present invention provides a pharmaceutical composition for skin-whitening containing resveratryl triglycolate or a pharmaceutically acceptable salt thereof as an active ingredient.

The composition of the present invention may contain resveratryl triglycolate or a cosmetically acceptable salt thereof as an active ingredient. The dosage form and the preparation method for the pharmaceutically acceptable salt is the same as the cosmetically acceptable salt described herein.

The pharmaceutical composition of the present invention may contain the active ingredient at from 0.01 wt % to 10 wt % of the whole composition, more ideally from 0.1 wt % to 10 wt %.

The pharmaceutical composition of the present invention may further contain a pharmaceutically acceptable excipient. As used herein, the term "pharmaceutically acceptable" means lacking toxicity to a cell or human. The carrier, without limitation, may include a buffer, preservative, pain-reducing agent, solubilizing agent, isotonic agent, stabilizing agent, base, excipient, and lubricant as long as they are known in the art. In addition, the pharmaceutical composition of the present invention may be formulated in an oral formulation such as a powder, granule, tablet, capsule, suspension, emulsion, syrup, and aerosol, an external application, a suppository, and a sterile injection solution. Further, the pharmaceutical composition may also be formulated in a topical medication such as an ointment, lotion, spray, patch, cream, powder, suspension, and gel. A carrier, excipient, and diluting agent, which may be contained in the composition of the present invention, may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The composition may be formulated by using a diluting agent or excipient such as a filler, extending agent, binder, wetting agent, disintegrating agent, and surfactant. A solid formulation for oral administration may be prepared by mixing at least one excipient selected from starch, calcium carbonate, sucrose, lactose, and gelatin. A lubricant such as magnesium stearate and talc may also be included. A liquid formulation for oral administration may include a suspension, solution, emulsion, or syrup, and may be prepared by using a simple diluting agent such as water and liquid paraffin, as well as various excipients, for example, a wetting agent, sweetener, air freshener, and preservative. A formulation for parenteral administration may include a sterilized aqueous solution, non-aqueous solvent, suspension, emulsion, lyophilized preparation, and suppository. The non-aqueous solvent and suspension may include vegetable oil such as propylene glycol, polyethylene glycol, and olive oil, and an injectable ester such as ethyl oleate. The suppository may be prepared by using witepsol, macrogol, tween 61, cacao butter, laurinum, and glycerogelatin.

As another aspect, the present invention provides a topical medication containing a pharmaceutical composition for skin-whitening.

As used herein, the term "topical medication" refers to a concept encompassing general applications for external use, and examples of formulation containing the pharmaceutical composition of the present invention may include a plaster, lotion, liniment, liquid and solution, aerosol, extract, ointment, fluid extract, emulsion, suspension, capsule, cream, soft and hard gelatin capsule, patch, and sustained-release formulation, but are not limited thereto.

The topical medication of the present invention may be a parenteral formulation prepared in a solid, semi-solid, or liquid dosage form with an inorganic or organic carrier, excipient, and diluting agent added. The parenteral administration of the present invention may be a transdermal application selected from the group consisting of a drop, ointment, lotion, gel, cream, patch, spray, suspension, and emulsion, but is not limited thereto.

The carrier, excipient, and diluting agent, which may be contained in the topical medication of the present invention, may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

The composition of the topical medication of each dosage form may include other components beside the composition of the present invention, and one of ordinary skill in the art may appropriately select and combine the components according to the formulation or purpose of use without difficulty, which may have a synergistic effect when simultaneously applied with another component.

As another aspect, the present invention provides a skin-whitening method including a composition including applying or administering resveratryl triglycolate or an acceptable salt thereof as an active ingredient to a subject.

Specifically, the composition of the present invention may include the active ingredient at from 0.01 wt % to 5 wt % of the whole composition.

Additionally, resveratryl triglycolate of the present invention specifically features an inhibition of melanin synthesis, and the inhibition of melanin synthesis is the same as previously described.

As used herein, the term "subject" refers to all animals including humans, in which a symptom due to pigmentation may have appeared or will appear, and the pigmentation in the skin may be improved, and the symptom may be fixed or recovered by applying the composition of the present invention to a subject. The pharmaceutical composition of the present invention may be used in parallel with the existing pharmaceutical composition for skin-whitening.

As used herein, the term "applying" refers to all methods of appropriately applying the composition of the present invention to the skin of the subject in order for the composition to be absorbed into the skin.

In a case where the composition is applied to a subject, the composition of the present invention may prevent or improve the pigmentation and fix or recover a pigmentation symptom in the skin. The symptom due to pigmentation may include stains, freckles, seborrheic keratosis (senile lentigo, liver spot), and hyperpigmentation preceded by inflammation or irritation.

As used herein, the term "administering" refers to all methods of appropriately providing a prescribed substance to a subject, and a route for administration may be any conventional route as long as the composition reaches the targeted skin area.

The administration of the present invention may be oral or parenteral, but parenteral administration may be preferably used, and applying to the skin is more preferable.

The dose of the active ingredient is generally between 0.001 µg/kg/day to about 2000 µg/kg/day. A more desirable dose is between 0.5 µg/kg/day to 2.5 µg/kg/day. The external administration may be administered once or multiple times per day.

Specifically, the composition of the present invention may be a cosmetic composition, and the cosmetic composition is the same as previously described.

The composition of the cosmetic composition may be formulated in a dosage form selected from the group consisting of an aqueous solution, ointment for external use, cream, foam, nutritive cosmetic water (milky lotion), softening cosmetic water (toner), pack, softening water, milky liquid, make-up base, essence, soap, an aqueous cleaning solution, bathing soap, sunscreen cream, sun oil, suspension, emulsion, paste, gel, lotion, powder, surfactant-containing cleansing, oil, powder foundation, emulsion foundation, wax foundation, patch, and spray, but the dosage form is not limited thereto.

Additionally, the present invention may refer to a skin-whitening method containing the composition further including a cosmetically acceptable carrier, and the cosmetically acceptable carrier is the same as previously described.

The cosmetic composition may contain one or more additives selected from the group consisting of water, surfactant, humectant, low-grade alcohol, chelating agent, germicide, anti-oxidant, preservative, dye, and fragrance, and is the same as previously described.

More specifically, the composition of the present invention may be a pharmaceutical composition, and the pharmaceutical composition is the same as previously described.

Additionally, the pharmaceutical composition may include a pharmaceutically acceptable excipient, and the pharmaceutically acceptable excipient is the same as previously described.

Additionally, in a case where the composition of the present invention is used as a pharmaceutical composition, a pharmaceutical supplement such as a preservative, stabilizer, wettable powder or emulsifier, salt and buffer for osmoregulation, and other therapeutically effective components may be further included, and may be formulated in a dosage form for parenteral administration according to a conventional method.

An actual dose of the active ingredient should be understood to be determined considering the severity of a symptom, a selected route of administration, the age, sex, weight, and physical condition of a subject, and other relative factors.

As another aspect, the present invention provides a compound having a skin-whitening effect, represented by Formula 1 below:

[Formula 1]

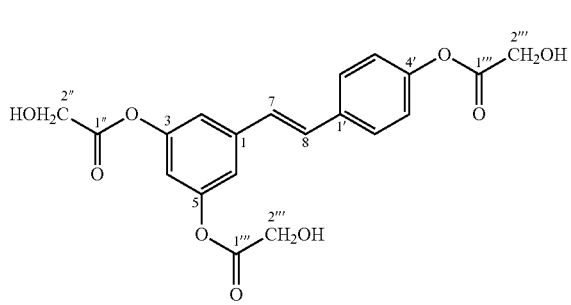

The compound having a skin-whitening effect, represented by Formula 1 above, is resveratryl triglycolate and is prepared by an esterification reaction.

As used herein, "esterification", for example, is a reaction in which a carboxylic acid is heated with an alcohol to yield an ester and water in the presence of an acid catalyst. The acid catalyst may include concentrated sulfuric acid, hydrochloric acid, or p-toluenesulfonic acid as well as dehydrated hydrogen chloride gas, but is not limited thereto. Since an esterification reaction is usually a slow and reversible reaction, inhibition of a reversible esterification reaction by continuously removing the water, the by-product, may improve the yield. In a case where the boiling point of the ester, the product, is lower than that of either the alcohol or the carboxylic acid, the reagent, a method in which the ester product is distilled away may be used to continue the reaction. The esterification reaction may be carried out using a method known in the art without limitation.

In an embodiment of the present invention, it was confirmed that resveratryl triglycolate reduced the melanin level in L-tyrosine-stimulated HEMs. It was also confirmed that resveratryl triglycolate inhibited an mRNA level and a protein expression level of tyrosinase (TYR), tyrosinase-related protein 1 (TYRP1), and L-3,4-dihydroxyphenylalanine-chrome tautomerase (DCT) stimulated with L-tyrosine, and suppressed those of microphthalmia-associated transcription factor (MITF) increased by treating L-tyrosine alone.

Advantageous Effect

In the present invention, resveratryl triglycolate inhibits melanin synthesis and expression of a gene related thereto, and may be effectively used as a cosmetic and pharmaceutical composition for skin-whitening.

DESCRIPTION OF DRAWINGS

FIG. 1 shows the chemical structures of resveratryl triglycolate (RTG), glycolic acid (GA), and resveratryl triacetate (RTA).

FIG. 2 shows effects of arbutin, resveratrol, resveratryl triglycolate (RTG), GA, and RTA on cell viability. Cells were treated with the five test compounds at the indicated concentrations for 48 hours. The data are shown as percentages of controls (mean±SE, n=3).

FIG. 3 shows effects of arbutin, resveratrol, resveratryl triglycolate (RTG), GA, and RTA on melanin synthesis in HEMs. The values for intra- and extracellular melanin levels were normalized with respect to total protein content. The data are shown as percentage of vehicle control (mean±SE, n=3). # $p<0.05$ vs. control. * $p<0.05$ vs. L-tyrosine treatment alone.

FIG. 4 shows effects of arbutin, resveratrol, resveratryl triglycolate (RTG), GA, and RTA on the mRNA expression corresponding to melanogenic enzymes in HEMs. HEMs were pre-treated with the test compounds at the indicated concentrations for 60 minutes, and then stimulated by adding 4.0 mM of L-tyrosine for 48 hours. The total cellular RNA was applied to qPCR analysis. The mRNA expression levels of TYR, TYRP1, and DCT were normalized with respect to values of GAPDH mRNA levels. The data are shown as percentage of vehicle control (mean±SE, n=3). # $p<0.05$ vs. control. * $p<0.05$ vs. L-tyrosine treatment alone.

FIG. 5 shows effects of arbutin, resveratrol, resveratryl triglycolate (RTG), GA, and RTA on melanogenic enzyme expression in HEMs. HEMs were pre-treated with the test compounds at the indicated concentrations for 60 minutes, and then stimulated by adding 4.0 mM of L-tyrosine for 48 hours. Whole cell lysates were applied to western blot analysis. The protein expression levels for TYR, TYRP1, and DCT were normalized with respect to values of GAPDH protein levels. The data are shown as percentage of vehicle control (mean±SE, n=3). # $p<0.05$ vs. control. * $p<0.05$ vs. L-tyrosine treatment alone.

FIG. 6 shows effects of arbutin, resveratrol, resveratryl triglycolate (RTG), GA, and RTA on the expression of MITF mRNA and protein in HEMs. HEMs were pre-treated with the test compounds at the indicated concentrations for 60 minutes, and then stimulated by adding 4.0 mM of L-tyrosine for 48 hours. The total cellular RNA was applied to qPCR analysis. The MITF expression levels were normalized with respect to values of GAPDH. The data are shown as percentage of vehicle control (mean±SE, n=3). # $p<0.05$ vs. control. * $p<0.05$ vs. L-tyrosine treatment alone.

FIG. 7 shows changes of visual assessment following 8 consecutive weeks' application of the products (mean±SD, * $p<0.05$ vs. before treatment, † $p<0.05$ vs. control group).

FIG. 8 shows changes of melanin index following 8 consecutive weeks' application of the products (mean±SD, * $p<0.05$ vs. before treatment, † $p<0.05$ vs. control group).

FIG. 9 shows changes of skin lightness (L*value) following 8 consecutive weeks' application of the products (mean±SD, *p<0.05 vs. before treatment, †p<0.05 vs. control group).

FIG. 10 shows changes of skin color (ITA° value) following 8 consecutive weeks' application of the products (mean±SD, *p<0.05 vs. before treatment, †p<0.05 vs. control group).

BEST MODE

Hereinafter, the present invention will be described in more detail with reference to the following examples, comparative examples, and experimental examples. However, the following examples, comparative examples, and experimental examples are provided for illustrative purposes only, and the scope of the present invention should not be limited thereto in any manner.

Example 1

Synthesis of Resveratryl Triglycolate (RTG)

Tetrahydropyran (THP)-protected glycolic acid (GA) was synthesized in the same manner as described in the reference (Costin G E, Faseb J 2007, 21:976-94). Esterification of resveratrol and THP-protected GA yielded (E)-5-(4-(2-(tetrahydro-2H-pyran-2-yloxy)acetoxy)styryl)-1,3-phenylene bis(2-(tetrahydro-2H-pyran-2-yloxy)acetate), using (1-Ethyl-3-(3-dimethylaminopropyl)carbodiimide) (EDC) as a dehydration agent, and 4-dimethylaminopyridine (DMAP) as a catalyst. The thus-obtained product was dissolved in dioxane and mixed with 2 N HO/ether to prepare resveratryl triglycolate as a white solid. Every step was confirmed by $^1$H and $^{13}$C NMR spectroscopy and mass spectrometry, and resveratryl triglycolate was obtained as an amorphous powder having the following properties. The properties are shown in Table 1.

UV (EtOH) $\lambda_{max}$ (log ε), 294 (4.24) nm; ESIMS (positive mode) m/z425 [M+Na]$^+$, 403 [M+H]$^+$, 345 [M−C2H2O2+H]$^+$, 287 [M−C4H4O4+H]$^+$, (negative mode) m/z 401 [M−H]$^-$, 344 [M−C2H2O2−H]$^-$, 285 [M−C4H4O4−H]$^-$; $^1$H-NMR (700 MHz, DMSO-d6); $^{13}$C-NMR (175 MHz, DMSO-d6)

A chemical identification of resveratryl triglycolate (RTG), was verified based on MS and NMR data. As a result resveratryl triglycolate (RTG), showed an [M+H]$^+$ ion peak at m/z 403 of the positive mode ESI-MS, corresponding to the molecular formula $C_{20}H_{18}O_9$. The $^1$H- and $^{13}$C-NMR spectra data showed the presence of one set of ortho-coupled aromatic protons assignable to a p-substituted benzene unit [$\delta_H$ 7.66 (2H, d, J=9.1 Hz, H-2', 6') and $\delta_C$ 127.5 (C-2', 6'); $\delta_H$ 7.18 (2H, d, J=9.1 Hz, H-3', 5') and $\delta_C$ 121.7 (C-3', 5')], three meta-coupled aromatic protons on a 1,3,5-trisubstituted benzyl moiety [$\delta_H$ 7.33 (2H, d, J=1.4 Hz, H-2, 6) and $\delta_C$ 116.8 (C-2, 6); $\delta_H$ 6.95 (1H, t, J=1.4 Hz, H-4) and $\delta_C$ 114.4 (C-4)], one pair of trans olefinic double bonds [$\delta_H$ 7.36 (1H, d, J=16.1 Hz, H-8) and $\delta_C$ 129.3 (C-8); $\delta_H$ 7.25 (1H, d, J=16.1 Hz, H-7) and $\delta_C$ 126.4 (C-7)], and three sets of GA moieties [$\delta_H$ 4.33 (4H, d, J=6.3 Hz, H-2", 2''') and 5.64 (2H, d, J=6.3 Hz, OH-2", 2'''), $\delta_C$ 171.0 (C-1", 1''') and 59.35 (C-2", 2'''); $\delta_H$ 4.31 (2H, d, J=6.3 Hz, H-2'''') and 5.60 (1H, d, J=6.3 Hz, OH-2''''), $\delta_C$ 171.2 (C-1'''') and 59.37 (C-2'''')].

All protonated carbons were confirmed by analysis of the heteronuclear single quantum coherence (HSQC) spectrum. The results indicated that the compound may have a resveratrol skeleton with three GA groups. Additionally, the locations of these GA groups were confirmed by observation of heteronuclear multiple bond correlation (HMCB). From H-3'/5' ($\delta_H$ 7.18) to C-1'''' ($\delta_C$ 171.2), from H-4 ($\delta_H$ 6.95) to C-1" and 1''' ($\delta_C$ 171.0), and from H-2/6 ($\delta_H$ 7.33) to C-1" and 1''' ($\delta_C$ 171.0). These correlations indicate three GA groups of C-3, 5, and 4' respectively. Thus, the structure of the compound is shown to be 3, 5, 4'-triglycolate-trans-stilbene or resveratryl triglycolate.

TABLE 1

| | RTG | | |
|---|---|---|---|
| position | $\delta_H$ mult., (J Hz) | $\delta_C$ mult. | HMBC |
| 1 | | 139.2 s | |
| 2 | 7.33 d (1.4) | 116.8 d | 1, 3, 5, 6, 7, 1" |
| 3 | | 150.6 s | |
| 4 | 6.95 t (1.4) | 114.4 d | 2, 3, 5, 6, 1", 1''' |
| 5 | | 150.6 s | |
| 6 | 7.33 d (1.4) | 116.8 d | 1, 2, 3, 5, 7, 1''' |
| 7 | 7.25 d (16.1) | 126.4 d | 1, 1', 8, 2, 6, |
| 8 | 7.36 d (16.1) | 129.3 d | 1, 1', 7, 2', 6' |
| 1' | | 133.9 s | |
| 2' | 7.66 d (9.1) | 127.5 d | 8, 3', 4', 5', 6' |
| 3' | 7.18 d (9.1) | 121.7 d | 1', 4', 5', 1'''' |
| 4' | | 149.6 s | |
| 5' | 7.18 d (9.1) | 121.7 d | 1', 3', 4', 1'''' |
| 6' | 7.66 d (9.1) | 127.5 d | 8, 2', 3', 4', 5' |
| 1" | | 171.0 s | |
| 2" | 4.33 d (6.3) | 59.35 t | 1" |
| 1''' | | 171.0 s | |
| 2''' | 4.33 d (6.3) | 59.35 t | 1''' |
| 1'''' | | 171.2 s | |
| 2'''' | 4.31 d (6.3) | 59.37 t | 1'''' |
| 2"-OH | 5.64 t (6.3) | | 1", 2" |
| 2'''-OH | 5.64 t (6.3) | | 1''', 2''' |
| 2''''-OH | 5.60 t (6.3) | | 1'''', 2'''' |

$^a$Measured at 700 and 175 MHz; obtained in DMSO-d$_6$ with TMS as an internal standard. The assignments were based on $^1$H-$^1$H COSY, HSQC, and HMBC experiments.

Example 2

Evaluation of Cytotoxicity of Resveratryl Triglycolate (RTG)

Example 2-1

Cell Culture

Human epidermal melanocytes (HEM) derived from neonatal human foreskins were purchased from Cascade Biologics (Portland, Oreg., USA). The HEMs were cultivated in Medium 254 supplemented with human melanocyte growth supplements (Cascade Biologics) and antibiotics.

Example 2-2

Method of Analysis

In order to analyze the cytotoxicity of resveratryl triglycolate (RTG), the resveratryl triglycolate (RTG) prepared in Example 2-1 was used, and the cytotoxicity was analyzed by trypan blue exclusion assay using arbutin, resveratrol, glycolic acid (GA), and resveratryl triacetate (RTA) as test compounds or comparative test compounds.

First, arbutin, resveratrol, resveratryl triglycolate (RTG), GA, and RTA were treated in HEMs at concentrations in the range of 3 μM to 1000 μM, detached from the culture plates by trypsinization, and then harvested by centrifugation at 1200×g for 3 minutes. The cells were then suspended in the culture medium and mixed with 0.1% trypan blue solution (Sigma-Aldrich) at a 1:1 ratio. The numbers of stained dead cells and unstained live cells were counted three times using a hemocytometer.

Example 2-3

Evaluation of Cytotoxicity

As a result of evaluation of the cytotoxicity, as shown in FIG. 2, resveratrol, resveratryl triglycolate (RTG), and RTA showed the same level of cytotoxicity as HEMs, barely showed cytotoxicity at concentrations below 30 μM, and showed cytotoxicity at concentrations above 30 μM. Arbutin and GA showed no cytotoxicity at concentrations of up to 1000 μM.

Example 3

Effect of Resveratryl Triglycolate on Inhibiting Melanin Synthesis

Example 3-1

Methods

In order to examine the effects of resveratryl triglycolate on melanin synthesis using HEMs, arbutin, resveratrol, resveratryl triglycolate (RTG), GA, and RTA were treated at concentrations of 3 μM and 10 μM for 60 minutes, and then stimulated with 4.0 mM L-tyrosine for 48 hours. The extracellular melanin levels were evaluated by measuring the absorbance of the conditioned media at a wavelength of 490 nm, while the intracellular melanin levels were evaluated after extracting melanin from the cells using 0.1 M NaOH at 60° C. for 60 minutes. The values for melanin content were normalized with respect to the protein content in each sample. The protein content was evaluated using the Bio-Rad DC assay (Bio-Rad Laboratories, Inc., Hercules, Calif., USA).

Example 3-2

Effects of Inhibiting Melanin Synthesis

Effects of resveratryl triglycolate (RTG) on inhibiting melanin synthesis were examined after adding 4 mM L-tyrosine, which stimulates melanin synthesis in HEMs, and as a result, as shown in FIG. 3, the intra- and extracellular melanin levels were increased by L-tyrosine treatment, and these increases were reduced by resveratryl triglycolate (RTG). These increases were also reduced by resveratrol and RTA, although the decreases were not as large as those by resveratryl triglycolate. Arbutin and GA showed no significant effect on melanin synthesis at concentrations of up to 10 μM.

Example 4

Effects of Melanogenic Enzymes of Resveratryl Triglycolate (RTG) on Inhibiting mRNA Expression

Example 4-1 qRT-PCR Analysis

In order to examine an effect of resveratryl triglycolate (RTG) on melanogenic enzyme expression in L-tyrosine-stimulated HEMs, first, the total mRNA was extracted, and the mRNA expression levels of TYR, TYRP1, and DCT were analyzed through qRT-PCR.

RNA was extracted using an RNeasy kit (Qiagen, Valencia, Calif., USA), and 1 μg of mRNA was prepared by reverse transcription using a High Capacity cDNA Archive Kit (Applied Biosystems, Foster City, Calif. USA). PCR was conducted in a reaction mixture solution (20 μL) containing SYBR® Green PCR Master Mix (Applied Biosystems), 60 μg of cDNA, and 2 pmol of gene-specific primer sets (Macrogen, Seoul), using a StepOnePlus™ Real-Time PCR System (Applied Biosystems). The primers used are shown in Table 2, primers of SEQ ID NO: 1 and SEQ ID NO: 2 were used for tyrosinase (TYR, GenBank accession number NM000372.3) extraction, the primers of SEQ ID NO: 3 and SEQ ID NO: 4 were used for tyrosinase-related protein 1 (TRP1, NM000550.1) extraction, and the primers of SEQ ID NO: 5 and SEQ ID NO: 6 were used for DOPA chrome tautomerase (DCT, NM001922.3) extraction. The reactions were conducted using the following protocol: the initial incubation at 50° C. for 2 minutes, DNA polymerase activation at 95° C. for 10 minutes, 40 cycles of denaturation and annealing at 95° C. for 15 seconds, and extension at 60° C. for 1 minute.

TABLE 21

| Gene | Primer | Sequence | SEQ ID NO |
|---|---|---|---|
| Tyrosinase (TYR) | forward primer | 5'-GATGAGTACATGGGAGGTCAGC-3' | 1 |
|  | reverse primer | 5'-GTACTCCTCCAATCGGCTACAG-3' | 2 |
| tyrosinase-related protein 1 (TYRP1) | forward primer | 5'-GCTCCAGACAACCTGGGATA-3' | 3 |
|  | reverse primer | 5'-TCAGTGAGGAGAGGCTGGTT-3' | 4 |
| DOPA chrome tautomerase (DCT) | forward primer | 5'-AGATTGCCTGTCTCTCCAGAAG-3' | 5 |
|  | reverse primer | 5'-CTTGAGAATCCAGAGTCCCATC-3' | 6 |

Example 4-2

Effects of Melanogenic Enzymes on Inhibiting mRNA Expression

Effects of resveratryl triglycolate (RTG) on mRNA expression of melanogenic enzymes were analyzed, as a result, as shown in FIG. 4, the mRNA expression levels of the melanogenic enzymes, TYR, TYRP1, and DCT, were increased by L-tyrosine treatment, and these increases were reduced by resveratryl triglycolate (RTG). These increases were also reduced by resveratrol and RTA, yet the decreases were not as large as those by resveratryl triglycolate (RTG). Additionally, arbutin and GA showed no effect on melanin synthesis at concentrations of up to 10 μM.

Example 5

Effects of Melanogenic Enzyme of Resveratryl Triglycolate (RTG) on Protein Expression

Example 5-1

Western Blot Analysis

In order to examine an effect of resveratryl triglycolate (RTG) on melanogenic enzyme expression, western blotting of HEM cell lysates was conducted. First, cells were lysed in a lysis buffer (lysis buffer, 10 mM Tris-Cl pH 7.2, 150 mM NaCl, 5 mM EDTA, 1% sodium dodecyl sulfate (SDS), 1% Triton X-100, 1% deoxycholate) supplemented with a 1 mM phenylmethylsulfonyl fluoride and protease inhibitor cocktail (Roche, Mannheim, Germany). After the lysates were mixed with Laemmli sample buffer, the proteins were denatured by heating at 95° C. for 5 minutes. Then the proteins were separated from gel containing 10% polyacrylamide by polyacrylamide gel electrophoresis (SDS-PAGE). Once separated by electrophoresis, the proteins were transferred to polyvinylidene difluoride membrane (Amersham Pharmacia, Little Chalfont, UK). The membranes were incubated overnight at 4° C. in a solution containing primary antibodies, and subsequently in a solution containing secondary antibodies conjugated with horseradish peroxidase (Cell Signaling, Danvers, Mass., USA) at room temperature for 1 hour. The primary antibodies of tyrosinase (TYR), TRP1, DCT, MITF, and GAPDH were purchased from Santa Cruz Biotechnology (Santa Cruz, Calif., USA). The immunoreactive bands were detected by using a picoEPD Western Reagent kit (ELPIS-Biotech, Daejeon, Korea), and densitometric analysis was performed using the NIH Image program.

Example 5-2

Effects of Melanogenic Enzymes on Protein Expression

Effects of resveratryl triglycolate (RTG) on melanogenic enzyme expression were analyzed, as a result, as shown in FIG. 5, the protein expression levels of TYR, TYRP1, and DCT, were increased by L-tyrosine treatment, and these increases were reduced by treatment of resveratryl triglycolate, RTA, or resveratrol. Resveratryl triglycolate showed the largest decreases, and resveratrol and RTA reduced the protein expression levels of TYR, TYRP1, and DCT as well, although the decreases were not as large as those by resveratryl triglycolate. Additionally, arbutin and GA showed no effect on protein expression of TYR, TYRP1, and DCT.

Additionally, in order to examine the mechanism of melanogenic enzyme regulations of resveratryl triglycolate, the expression levels of mRNA and protein of microphthalmia-associated transcription factor (MITF) were examined if affected by resveratryl triglycolate. As a result, as shown in FIG. 6, the expression levels of mRNA and protein were both increased, and these increases were largely reduced by resveratryl triglycolate. These increases were also reduced by resveratrol and RTA, although the decreases were not as large as those by resveratryl triglycolate. Additionally, arbutin and GA showed no effect on MITF expression at concentrations of up to 10 μM.

Example 6

Evaluation of Human Body Skin-Whitening Effect

Example 6-1

Selection of Test Subjects

The clinical test was conducted with 22 female subjects aged 18 to 60 who met the eligibility criteria, but not the exclusion criteria. Those who had a Fitzpatrick skin type of III or IV and were interested in participating in the test were provided with information about the purpose and the methods of the test as well as expected efficacies and adverse reactions, signed a consent form, and then participated in the test.

Volunteers who met the following eligibility criteria were selected as a test subject group.

(1) Women aged 18 to 60 with a skin type of III or IV, (2) Volunteers who fully understood and agreed to the purpose and content of the experiment and voluntarily signed the written consent form before the experiment, (3) Those observable and traceable for the follow-up period Additionally, as the exception criteria, volunteers with a specific skin disease were excluded, and the subjects were not allowed to use any functional cosmetics or pharmaceutical products other than the test products.

Example 6-2

Skin Characteristics of the Subjects

The skin characteristics of the subjects were investigated by conducting a survey, and the results are as follows (Table 3 and Table 4).

TABLE 3

Skin characteristics of volunteers (n = 22)

| Item | Classification | Frequency (N) | Percentage (%) |
|---|---|---|---|
| Age | 20s | 2 | 9.09 |
|  | 30s | 5 | 22.73 |
|  | 40s | 15 | 68.18 |
| Skin type | Dry | 6 | 27.27 |
|  | Normal | 11 | 50.00 |
|  | Oily | 0 | 0.00 |
|  | Dry and oily | 5 | 22.73 |
|  | Problematic | 0 | 0.00 |

TABLE 4

Skin condition of volunteers by skin physiological factors (n = 22)

| Item | Classification | Frequency (N) | Percentage (%) |
|---|---|---|---|
| Hydration | Sufficient | 1 | 4.55 |
|  | Normal | 12 | 54.55 |
|  | Deficient | 9 | 40.91 |
| Sebum | Glossy | 3 | 13.64 |
|  | Normal | 14 | 63.64 |
|  | Deficient | 5 | 22.73 |
| Surface | Smooth | 3 | 13.64 |
|  | Normal | 17 | 77.27 |
|  | Rough | 2 | 9.09 |
| Thickness | Thin | 6 | 27.27 |
|  | Normal | 16 | 72.73 |
|  | Thick | 0 | 0.00 |
| Duration of UV exposure | Less than 1 hr | 5 | 22.73 |
|  | 1 to 3 hrs | 15 | 68.18 |
|  | More than 3 hrs | 2 | 9.09 |
| Occurrence frequency of hyper-pigmentation | Little | 0 | 0.00 |
|  | Normal | 15 | 68.18 |
|  | Well | 7 | 31.82 |
| Smoking | No | 22 | 100.00 |
|  | Less than 10 pieces | 0 | 0.00 |
|  | More than 10 pieces | 0 | 0.00 |
| Irritability | Yes | 3 | 13.64 |
|  | No | 19 | 86.36 |
| Stinging | Yes | 0 | 0.00 |
|  | No | 22 | 100.00 |
| Adverse reaction | Yes | 0 | 0.00 |
|  | No | 22 | 100.00 |

Example 6-3

Induction of Artificial Pigmentation

Artificial pigmentation was induced by having forearms exposed to UVA+B, determining a minimal erythema dose (MED), and then having the forearms exposed to UV(UVA+B) 2 to 4.5 times stronger than MED.

Example 6-4

Test Products and Method of Use

As test products, product C containing 0.4% resveratryl triglycolate as an active ingredient, product B containing grape stem extracts, and product A containing no active ingredient were used. The composition of each product is as follows (Table 5).

TABLE 5

| Rx | Name of Component | Product A | Product B | Product C |
|---|---|---|---|---|
| A | Water | 56.94 | 3.82 | 53.42 |
|  | Phenoxyethanol | 0.3 | 0.3 | 0.3 |
|  | 1,2-Hexanediol | 2 | 2 | 2 |
|  | EDTA-4Na | 0.08 | 0.08 | 0.08 |
| $A_1$ | Grape stem extract |  | 50 |  |
| $A_2$ | Na-Hyaluronate (1%) | 5 | 5 | 5 |
|  | Distilled water | 5 | 5 | 5 |
| $A_3$ | Cabopol #940(2%) | 0.34 | 0.4 | 0.4 |
|  | Distilled water | 17 | 20 | 20 |
| B | 1.3-B.G | 4 | 4 | 4 |
|  | Polysorbate 60 |  |  | 0.9 |
|  | RTG |  |  | 0.4 |
| C | Glycerine | 2 | 2 | 2 |
|  | Polysorbate 60 | 1.8 | 1.8 | 0.9 |
|  | Perfume | 0.1 | 0.1 | 0.1 |
| D | Hydrolyzed collagen | 0.1 | 0.1 | 0.1 |
| E | Triethanolamine | 0.34 | 0.4 | 0.4 |
|  | Distilled water | 5 | 5 | 5 |
|  | TOTAL | 100 | 100 | 100 |

As a method of product use, the test subject group was made to apply each of products A, B, and C on the test area (forearm), twice daily for 8 weeks after the artificial pigmentation. The subjects were divided into three groups through block randomization. Group A applied the products in the order of A, B, and C from the top, and group B applied the products in the order of B, C, and A from the top, whereas group C applied the products in the order of C, A, and B from the top. The test was conducted in three groups, but the results of product A (test group) and C (control group) were described as below. The result of the product B was omitted due to its low relevance to the present patent.

Example 6-5

Analysis of Visual Evaluation of Artificial Pigmented Area of Skin

Visual assessment was independently conducted by two testers, rating the degree of pigmentation on a scale from 0 to 10 (0, bright and transparent; ~9, dark and dull, in increments of 0.5), and then averaging the values.

Observations were compared and analyzed before and after each evaluation point, the degree of pigmentation for both the test group and the control group showed significant improvement after two weeks of use of the products ($p<0.05$, Table 6, FIG. 7).

TABLE 6

Statistical analysis of visual assessment

| Group | Week | N | Mean[1] | SD | p-value[2] |
|---|---|---|---|---|---|
| Control | Before | 22 | 7.05 | 0.49 | — |
| (A) | 2 W | 22 | 6.82 | 0.42 | 0.000* |
|  | 4 W | 22 | 6.53 | 0.40 | 0.000* |
|  | 6 W | 22 | 5.83 | 0.47 | 0.000* |
|  | 8 W | 22 | 4.98 | 0.65 | 0.000* |
| Test | Before | 22 | 7.11 | 0.41 | — |
| (C) | 2W | 22 | 6.93 | 0.44 | 0.002* |
|  | 4 W | 22 | 6.48 | 0.39 | 0.000* |
|  | 6 W | 22 | 5.73 | 0.45 | 0.000* |
|  | 8 W | 22 | 4.84 | 0.67 | 0.000* |

[1]Decrement of the mean-value represents improvement of hyperpigmentation.
[2]Significantly different at *$p < 0.05$ compared with before treatment.

Additionally, observations of the pigmentations were compared and analyzed before and after each evaluation point. The pigmentation for the test group showed a significant improvement after 6 weeks and 8 weeks of product use, compared to the control group ($p<0.05$, Table 7, FIG. 7).

TABLE 7

Statistical analysis of visual assessment between test and control groups

| Group | 2 W | 4 W | 6 W | 8 W |
|---|---|---|---|---|
| Test vs. Control | 0.463 | 0.102 | 0.028* | 0.012* |

*Significantly different at $p < 0.05$ compared with control group.

Example 6-6

Melanin Index Analysis using Absorbance and Reflection

Mexameter® MX18 (C+K, Germany) was used for melanin index measurement. This is a tool to measure the levels of melanin and hemoglobin, key factors of skin color determination, based on absorbance and reflection. The skin absorption rates of each wavelength were digitalized and measured as melanin index (MI) and erythema index (EI). These measurements were repeated three times on the pigmented skin area and averaged.

Observations of the MI were compared and analyzed before and after each evaluation point, and the MI for the both test group and control group showed a significant improvement after two weeks of product use ($p<0.05$, Table 8, FIG. 8).

TABLE 8

Statistical analysis of melanin index by absorption and reflection

| Group | Week | N | Mean[1] | SD | p-value[2] |
|---|---|---|---|---|---|
| Control | Before | 22 | 204.89 | 34.43 | — |
| (A) | 2 W | 22 | 191.08 | 33.64 | 0.000* |
|  | 4 W | 22 | 188.41 | 32.49 | 0.000* |
|  | 6 W | 22 | 179.73 | 31.45 | 0.000* |
|  | 8 W | 22 | 172.38 | 32.62 | 0.000* |
| Test | Before | 22 | 204.67 | 34.33 | — |
| (C) | 2 W | 22 | 194.55 | 34.12 | 0.000* |
|  | 4 W | 22 | 187.94 | 35.49 | 0.000* |
|  | 6 W | 22 | 168.96 | 32.18 | 0.000* |
|  | 8 W | 22 | 163.17 | 32.77 | 0.000* |

[1]Decrement of the mean-value represents decrease of melanin index.
[2]Significantly different at *$p < 0.05$ compared with before treatment.

Additionally, observations of the MI were compared and analyzed before and after each evaluation point. The MI for the test group showed a significant improvement after 6 weeks and 8 weeks of product use compared to the control group ($p<0.05$, Table 9, FIG. 8).

TABLE 9

Statistical analysis of melanin index between test and control groups

| Group | 2 W | 4 W | 6 W | 8 W |
|---|---|---|---|---|
| Test vs. Control | 0.027 | 0.885 | 0.000* | 0.000* |

*Significantly different at $p < 0.05$ compared with control group.

Example 6-7

Analysis of Skin Luminance (L*value) and Individual Typology Angle (ITA° value)

Spectrophotometer® CM-2500d (Minolta, Japan) was used to measure skin lightness and an individual typology angle. This is a tool to measure spectral reflection of object color in L*, a*, and b* parameters, the color coordinates of CIE, by measuring tristimulus values. L* represents the lightness, and a* and b* represent the color and the chroma. a* indicates the red while −a* indicates the green, and b* indicates yellow while −b* indicates blue. The values of L*, a*, and b* toward the middle indicate achromatic colors while those to the opposite directions indicate high chromaticity. These measurements were repeated three times on the pigmented skin area, and the average value was used to analyze the L* value. The ITA° value was analyzed using the following equation.

L*: Luminance parameters (brightness)

a*: Chrominance parameters (green-to-red)

b*: Chrominance parameters (blue-to-yellow)

ITA°=[Arc Tangent ((L*−50)/b*)]180/3.14159

Additionally, for the L* value using spectral reflection, observations were compared and analyzed before and after each evaluation point. The L* value for the test group showed a significant improvement after 6 weeks and 8 weeks of product use compared to the control group (p<0.05, Table 11, FIG. 9).

TABLE 10

Statistical analysis of skin lightness (L* value) by spectral reflectance

| Group | Week | N | Mean[1] | SD | p-value[2] |
|---|---|---|---|---|---|
| Control | Before | 22 | 61.20 | 2.30 | — |
| (A) | 2 W | 22 | 62.53 | 2.19 | 0.000* |
|  | 4 W | 22 | 62.86 | 2.23 | 0.000* |
|  | 6 W | 22 | 63.54 | 2.36 | 0.000* |
|  | 8 W | 22 | 63.88 | 2.10 | 0.000* |
| Test | Before | 22 | 61.05 | 2.56 | — |
| (C) | 2 W | 22 | 62.23 | 2.20 | 0.002* |
|  | 4 W | 22 | 62.88 | 2.26 | 0.000* |
|  | 6 W | 22 | 64.08 | 2.51 | 0.000* |
|  | 8 W | 22 | 64.59 | 2.38 | 0.000* |

[1]Increment of the mean-value represents improvement of skin lightness (L* value).
[2]Significantly different at *p < 0.05 compared with before treatment.

Additionally, for the L* value using spectral reflection, observations were compared and analyzed before and after each evaluation point. The L* value for the test group showed a significant improvement after 6 weeks and 8 weeks of product use compared to the control group (p<0.05, Table 11, FIG. 9).

TABLE 11

Statistical analysis of skin lightness (L* value) between test and control groups

| Group | 2 W | 4 W | 6 W | 8 W |
|---|---|---|---|---|
| Test vs. Control | 0.234 | 0.344 | 0.000* | 0.000* |

*Significantly different at p < 0.05 compared with control group.

Meanwhile, for the ITA° value using spectral reflection, observations were compared and analyzed before and after each evaluation point. The ITA° value for the both test group and the control group showed a significant improvement after two weeks of product use (p<0.05, Table 12, FIG. 10).

TABLE 12

Statistical analysis of skin color (ITA° value) by spectral reflectance

| Group | Week | N | Mean[1] | SD | p-value[2] |
|---|---|---|---|---|---|
| Control | Before | 22 | 29.47 | 5.16 | — |
| (A) | 2 W | 22 | 31.74 | 5.00 | 0.000* |
|  | 4 W | 22 | 32.83 | 5.25 | 0.000* |
|  | 6 W | 22 | 34.72 | 5.40 | 0.000* |
|  | 8 W | 22 | 35.97 | 5.38 | 0.000* |
| Test | Before | 22 | 29.11 | 6.02 | — |
| (C) | 2 W | 22 | 31.54 | 5.11 | 0.001* |
|  | 4 W | 22 | 33.11 | 5.53 | 0.000* |
|  | 6 W | 22 | 36.22 | 6.07 | 0.000* |
|  | 8 W | 22 | 37.54 | 5.95 | 0.000* |

[1]Increment of the mean-value represents improvement of skin color (ITA° value).
[2]Significantly different at *p < 0.05 compared with before treatment.

Additionally, for the ITA° value using spectral reflection, observations were compared and analyzed before and after each evaluation point. The ITA° value for the test group showed a significant improvement after 6 weeks and 8 weeks of product use compared to the control group (p<0.05, Table 13, FIG. 10).

TABLE 13

Statistical analysis of skin lightness (L* value) between test and control groups

| Group | 2 W | 4 W | 6 W | 8 W |
|---|---|---|---|---|
| Test vs. Control | 0.659 | 0.174 | 0.000* | 0.000* |

*Significantly different at p < 0.05 compared with control group.

Example 6-8

Evaluation of Skin Safety

Medical examinations, observations of the test conductor, evaluations of subjects' subjective degree of skin stimulus, and objective skin stimulus were conducted at each evaluation point, and no adverse reactions were observed in all subjects during the entire experiment period (Table 14).

TABLE 14

Skin adverse reactions

| | Symptom | 2 W A/C | 4 W A/C | 6 W A/C | 8 W A/C |
|---|---|---|---|---|---|
| Subjective initation | Itching | 0 | 0 | 0 | 0 |
|  | Prickling | 0 | 0 | 0 | 0 |
|  | Tickling | 0 | 0 | 0 | 0 |
|  | Burning | 0 | 0 | 0 | 0 |
|  | Stinging | 0 | 0 | 0 | 0 |
|  | Stiffness | 0 | 0 | 0 | 0 |
|  | Tightening | 0 | 0 | 0 | 0 |
|  | etc. | 0 | 0 | 0 | 0 |
| Objective Irritation | Erythema | 0 | 0 | 0 | 0 |
|  | Edema | 0 | 0 | 0 | 0 |
|  | Scale | 0 | 0 | 0 | 0 |
|  | Papule | 0 | 0 | 0 | 0 |
|  | etc. | 0 | 0 | 0 | 0 |
| Total number of subjects | | 0 | 0 | 0 | 0 |

A; Control group,
C; Test group

Based on the above description, it should be understood by one of ordinary skill in the art that other specific embodiments may be employed in practicing the invention without departing from the technical idea or essential features of the present invention. In this regard, the above-described examples are for illustrative purposes only, and the invention is not intended to be limited by these examples. The scope of the present invention should be understood to include all of the modifications or modified forms derived from the meaning and scope of the following claims or its equivalent concepts, rather than the above detailed description.

The invention claimed is:

1. A compound represented by Formula 1 below:

[Formula 1]

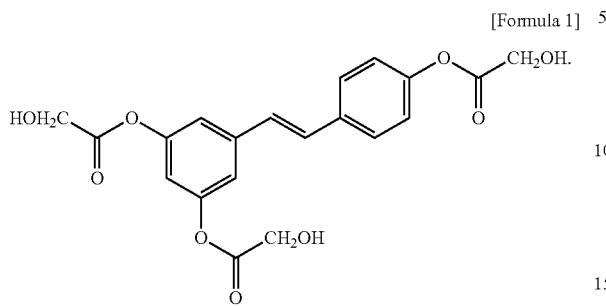

2. A cosmetic composition comprising the compound of claim 1.

3. A pharmaceutical composition comprising the compound of claim 1.

4. A method for skin-whitening comprising:
applying or administering a composition comprising resveratryl triglycolate, represented by Formula I below, or an acceptable salt thereof as an active ingredient to a subject:

[Formula 1]

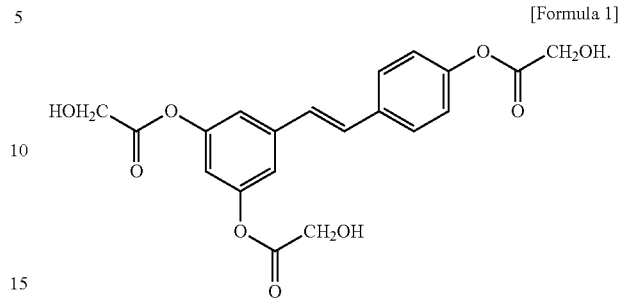

5. The method of claim 1, wherein the resveratryl triglycolate or an acceptable salt thereof is comprised at from 0.01 wt % to 5 wt %.

6. The method of claim 1, wherein the composition is a cosmetic composition.

7. The method of claim 1, wherein the composition is a pharmaceutical composition.

* * * * *

```
                              SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: tyrosinase-F primer

<400> SEQUENCE: 1
gatgagtaca tgggaggtca gc                                                  22

<210> SEQ ID NO 2
<211> LENGTH: 22
<212> TYPE: DNA
<213> ORGANISM: Artificial Sequence
<220> FEATURE:
<223> OTHER INFORMATION: tyrosinase-R primer

<400> SEQUENCE: 2
gtactcctcc aatcggctac ag                                                  22

<210> SEQ ID NO 3
<211> LENGTH: 20
<212> TYPE: DNA
<213> ORGANISM: Artificial Sequence
<220> FEATURE:
<223> OTHER INFORMATION: TYRP1-F primer

<400> SEQUENCE: 3
gctccagaca acctgggata                                                     20

<210> SEQ ID NO 4
<211> LENGTH: 20
<212> TYPE: DNA
<213> ORGANISM: Artificial Sequence
<220> FEATURE:
<223> OTHER INFORMATION: TYRP1-R primer

<400> SEQUENCE: 4
tcagtgagga gaggctggtt                                                     20

<210> SEQ ID NO 5
<211> LENGTH: 22
<212> TYPE: DNA
<213> ORGANISM: Artificial Sequence
<220> FEATURE:
<223> OTHER INFORMATION: DCT-F primer

<400> SEQUENCE: 5
agattgcctg tctctccaga ag                                                  22

<210> SEQ ID NO 6
<211> LENGTH: 22
<212> TYPE: DNA
<213> ORGANISM: Artificial Sequence
<220> FEATURE:
<223> OTHER INFORMATION: DCT-R primer

<400> SEQUENCE: 6
cttgagaatc cagagtccca tc                                                  22
```